(12) United States Patent
Raman (10) Patent No.: US 9,721,068 B2
(45) Date of Patent: Aug. 1, 2017

(54) SYSTEM AND METHOD FOR PROVIDING EVIDENCE-BASED EVALUATION

(71) Applicant: Verizon Patent and Licensing Inc., Arlington, VA (US)

(72) Inventor: Madhusudan Raman, Sherborn, MA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 459 days.

(21) Appl. No.: 14/327,372

(22) Filed: Jul. 9, 2014

(65) Prior Publication Data

US 2016/0012341 A1 Jan. 14, 2016

(51) Int. Cl.
*G06N 5/00* (2006.01)
*G06F 1/00* (2006.01)
*G06F 19/00* (2011.01)
*G06N 5/02* (2006.01)

(52) U.S. Cl.
CPC ........ *G06F 19/345* (2013.01); *G06F 19/3443* (2013.01); *G06N 5/025* (2013.01)

(58) Field of Classification Search
CPC ......... G06Q 10/06; G06Q 40/01; G06N 7/005
See application file for complete search history.

(56) References Cited

U.S. PATENT DOCUMENTS

| | | | |
|---|---|---|---|
| 2009/0254572 A1* | 10/2009 | Redlich | G06Q 10/06 |
| 2013/0138457 A1* | 5/2013 | Ragusa | G06Q 50/24 705/3 |
| 2013/0304506 A1* | 11/2013 | Gallivan | G06F 19/3431 705/3 |

\* cited by examiner

*Primary Examiner* — Stanley K Hill
*Assistant Examiner* — Kalpana Bharadwaj (57) ABSTRACT

An approach is provided for determining associations and/or propensity among the word occurrences during a therapy interaction for supporting a procedure. The approach involves parsing captured therapy interaction data to identify one or more word occurrences. The approach also involves determining one or more associations among the one or more word occurrences using a fuzzy association analysis and deep belief networks. The approach further involves determining a propensity of the one or more associations based on a probability analysis. The approach also involves specifying the one or more associations as evidence data for supporting a therapeutic outcome, a mental state classification, or a combination thereof.

20 Claims, 10 Drawing Sheets

SYSTEM AND METHOD FOR PROVIDING EVIDENCE-BASED EVALUATION

BACKGROUND INFORMATION

The process of mental health diagnosis and/or prognosis is typically based on a patient's self-reported experiences and observed behavior. This is one of the reasons mental health is frequently misdiagnosed. Misdiagnosis may involve failing to recognize the presence of a mental health condition, identifying a disorder when none is present, or mistaking the diagnosis for another condition. The fuzziness lies in the fact that the patients have a sense of state which may or may not be absolute information from a therapist perspective. Though other area of healthcare may have certain level of specificity, such complexity has caused mental health diagnosis and prognosis to be more challenging.

In terms of patient and healthcare, it is about how optimal a particular procedure is for a patient. In evidence based practice (EBP), an outcome of a particular procedure may be clearly identified, and may be collected for making decisions with regards to the care of an individual patient. However, there is no industry implementation of an EBP service, wherein a readily available service is provided in a business to provider to the consumer (B2P2C) manner.

Based on the foregoing, there is a need for offering on-demand EBP service as a managed cloud based service to enhance the state of mental healthcare.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF THE PREFERRED EMBODIMENT

An apparatus, method, and software for determining associations and/or propensity among the word occurrences during a therapy interaction for supporting a procedure, is described. In the following description, for the purposes of explanation, numerous specific details are set forth in order to provide a thorough understanding of the present invention. As is well known, the present invention may be practiced without these specific details or with an equivalent arrangement. In other instances, well-known structures and devices are shown in block diagram form in order to avoid unnecessarily obscuring the present invention.

Although various embodiments are described with respect to providing cloud based services pertaining to cognitive behavior therapy (CBT) and dialectical behavior therapy (DBT) for mental wellness, it is contemplated that the embodiments described herein are applicable to any disease or health condition that can be modeled according the example processes described below and can benefit from the EBP.

As discussed, there is a need for EBP services in an automated fashion. In one scenario, a machine scoring solution involves collecting data from an EBP service to determine whether a particular procedure succeeded. The method involves monitoring the progression of at least one procedure for a particular patient over a period of time, and then scoring that solution. In one scenario, there may be a degree of progression with regards to a functioning of a procedure, for example, a degree of 0 or 1, and the fractional values between 0 and 1 may be referred to as fuzziness. As noted above, the field of healthcare diagnosis and prognosis can be challenging even for healthcare professionals with high levels of expertise. For example, in the context of mental disease, a part of the fuzziness has to do with the fact that the patients have a sense of state which may or may not be absolute information from a therapist perspective, and the therapist needs to research in a fuzzy fashion to identify how the patient is really progressing. This is ambiguous, and trying to solve an ambiguity problem is a challenge in itself. As a result, there is an anticipated large increase in the need for offering on-demand evidence EBP service as a managed cloud based service.

Figure 1:
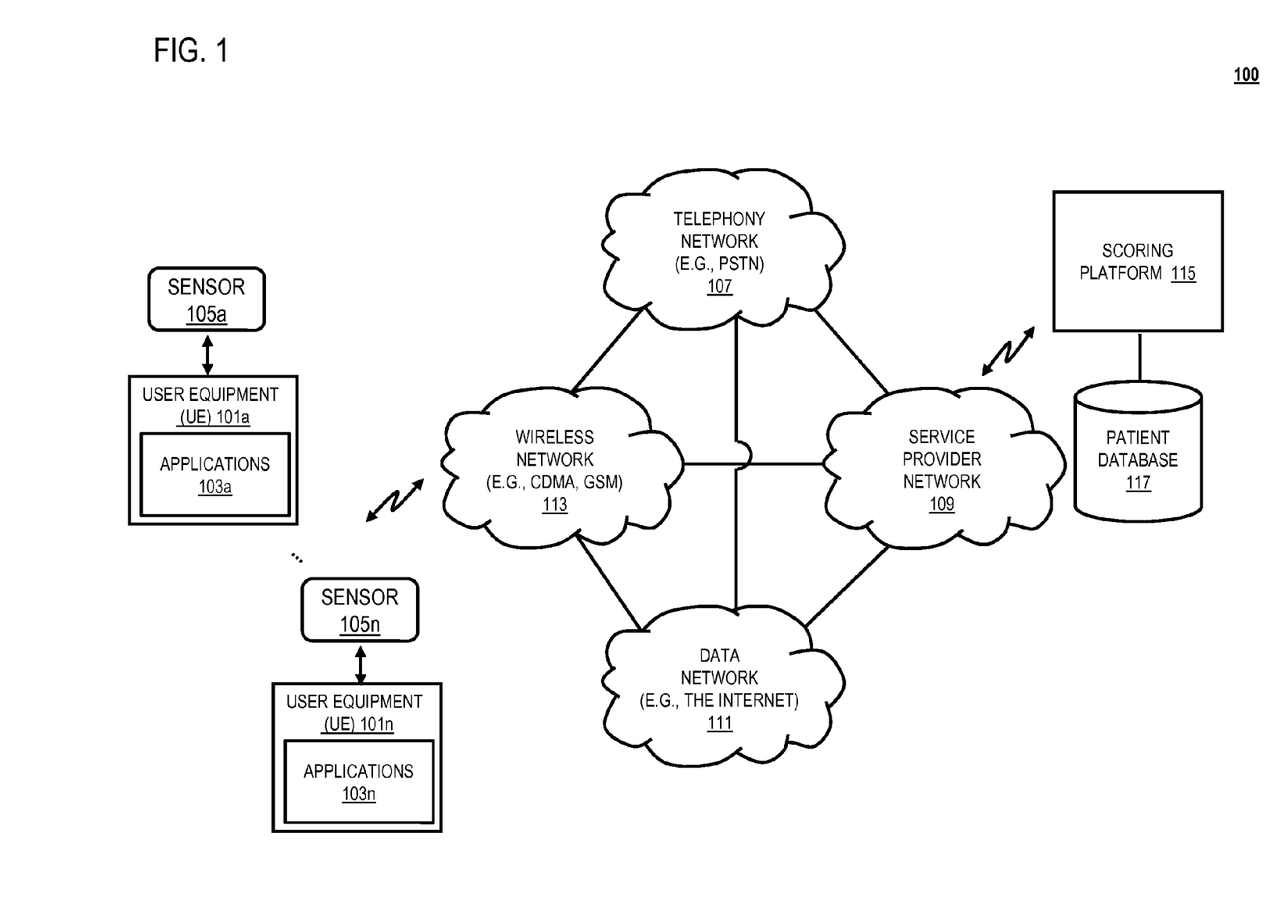
FIG. 1 is a diagram of a system capable of determining associations and/or propensity among the word occurrences during a therapy interaction for supporting a procedure, according to one embodiment.

To address the need, a system 100 of FIG. 1 introduces a system that provides diagnosis and prognosis services via a cloud based mechanism. The use of the system 100 can reduce the burden on health professionals (or on consumers themselves if permitted by regulatory authorities) to obtain disease diagnoses and/or prognoses, thereby making a positive impact on the cost and quality of healthcare. For example, use of healthcare services or healthcare classification systems such as system 100 can help in increasing accuracy and reliability of diagnoses, minimizing possible errors, as well as making the diagnoses more time efficient.

In one embodiment, the system 100 follows a multi-step process for setting up a healthcare service and delivering the service via the cloud. For example, the multi-step process may include any combination of the following steps: (1) processing of data during a therapy interaction, (2) parsing the data set, (3) performing association analysis of the data sets, (4) generating rules, (5) setting up the service, and (6) using the service. In one scenario, the scoring platform 115 via service provider network 109 (e.g., a cloud service) starts the process of preparation or aggregation of the data set of the clinical population data in the patient database 117 covering, e.g., healthy and/or diseased individuals. In one embodiment, the clinical population data is anonymized to protect the privacy of the individuals.

In one embodiment, the scoring platform 115 may explore the data collated for a specific mental disease. In one embodiment, as part of data exploration, the system 100 performs variables optimization where statistical tests (e.g., data distributions associated with the variables) are performed to identity words occurrences during a therapy interaction between a patient and a service provider. In one embodiment, the variables refer to healthcare or clinical readings or observations from a device 101 (e.g., a clinical device or a user device if permitted by regulatory authorities) and/or health application 103 executing on the device 101. For example, if the statistical tests indicate that there is either redundant benefits in including a specific variable or on the other hand no or little correlation between a variable and the disease or health classification of interest, then the variable can be dropped. In one scenario, fuzzy association propensity survival (FAPS) scoring is a statistical procedure that associates a treatment with other treatments, and provides a probability associated with the rules that can be extracted from the treatment. For example, memory loss, difficulties with abstract thinking, and inappropriate behavior may be the symptoms for dementia among 100 patients, then it may become a rule for determining dementia among future patients. In such manner, rather than recommending that a particular procedure works and the other procedure does not work, the system 100 may recommend that a particular procedure works under certain circumstances. This involves determining the efficiency and predicting the expected outcome of a treatment. Further, the temporal aspect of fuzziness relates to the probability on whether a particular treatment is going to work better within a certain time frame. In one example use case, a patient may use the device 101 to connect to the FAPS scoring web server via wireless connections. Then, a computer and/or a mobile device based dialogue, i.e., DBT and/or CBT may occur. An association transpires wherein a mobile device provides a DBT and/or CBT interface to the patient receiving mental care, and during the conversation, a natural language processing happens wherein a fuzzy association of terms creates the score for how the mental wellness of the patient is progressing.

In one scenario, an on-demand instantiation of a computational platform for supporting EBP may enhance the state of healthcare and wellness research. Further, FAPS scoring is a new technique introduced specifically for conversational associations to aid in the prognosis scoring of CBT and/or DBT therapy recipients. The managed service nature of the EBP setup supports low capital investment alongside significant gains. In addition, the EBP service may automatically trace and reference causal outcome associated with prognosis during the therapy. Further, the automated de-identification in this setting is also a novel use for evidence validation purposes. In such manner, FAPS scoring aids human therapists leverage EBP as a service, thereby allowing more precise diagnoses and increasingly targeted and effective interventions.

As shown in FIG. 1, the system 100 comprises user equipment (UE) 101a-101n (collectively referred to as UE 101) that may include or be associated with applications 103a-103n (collectively referred to as applications 103) and sensors 105a-105n (collectively referred to as sensors 105). In one embodiment, the UE 101 has connectivity to the scoring platform 115 via networks 107-113. In one embodiment, the scoring platform 115 performs one or more functions associated with determining associations and/or propensity among the word occurrences during a therapy interaction for supporting a procedure.

By way of example, the UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, or any combination thereof, including the accessories and peripherals of these devices, or any combination thereof. It is also contemplated that the UE 101 can support any type of interface to the user (such as "wearable" circuitry, etc.).

By way of example, the applications 103 may be any type of application that is executable at the UE 101, such as media player applications, social networking applications, calendar applications, content provisioning services, location-based service applications, navigation applications and the like. In one embodiment, the application 103 is a business-to-provider-to-consumer (B2P2C) application, a point of interaction for the care giver. By way of example, the B2P2C application 103 can have an extensive set of features including: (1) application issuance and on-boarding support; (2) real-time and post-consultative analysis; (3) clinical data archiving; (4) near-real time scoring; (5) visual and spoken (e.g., text-to-speech) feedback; (6) traditional disease risk calculators; (7) referenced output scores showing clinical references; etc. Although the application 103 is described as a B2P2C application, it is contemplated that the application 103 may also be a consumer facing application if permitted or approved by regulatory authorities. In one embodiment, the B2P2C EBP service is deployable as a software as a service (SaaS) instance.

By way of example, the sensors 105 may be any type of sensor. In certain embodiments, the sensors 105 may include, for example, a network detection sensor for detecting wireless signals or receivers for different short-range communications (e.g., Bluetooth, Wi-Fi, Li-Fi, near field communication etc.), temporal information, a camera/imaging sensor for gathering image data, an audio recorder for gathering audio data, and the like.

For illustrative purposes, the networks 107-113 may be any suitable wireline and/or wireless network, and be managed by one or more service providers. For example, telephony network 107 may include a circuit-switched network, such as the public switched telephone network (PSTN), an integrated services digital network (ISDN), a private branch exchange (PBX), or other like network. Wireless network 113 may employ various technologies including, for example, code division multiple access (CDMA), enhanced data rates for global evolution (EDGE), general packet radio service (GPRS), mobile ad hoc network (MANET), global system for mobile communications (GSM), Internet protocol multimedia subsystem (IMS), universal mobile telecommunications system (UMTS), etc., as well as any other suitable wireless medium, e.g., microwave access (WiMAX), wireless fidelity (Wi-Fi), satellite, and the like. Meanwhile, data network 111 may be any local area network (LAN), metropolitan area network (MAN), wide area network (WAN), the Internet, or any other suitable packet-switched network, such as a commercially owned, proprietary packet-switched network, such as a proprietary cable or fiber-optic network.

Although depicted as separate entities, networks 107-113 may be completely or partially contained within one another, or may embody one or more of the aforementioned infrastructures. For instance, the service provider network 109 may embody circuit-switched and/or packet-switched networks that include facilities to provide for transport of circuit-switched and/or packet-based communications. It is further contemplated that networks 107-113 may include components and facilities to provide for signaling and/or bearer communications between the various components or facilities of system 100. In this manner, networks 107-113 may embody or include portions of a signaling system 7 (SS7) network, or other suitable infrastructure to support control and signaling functions.

In one embodiment, the scoring platform 115 may be a platform with multiple interconnected components. The scoring platform 115 may include multiple servers, intelligent networking devices, computing devices, components and corresponding software for determining associations and/or propensity among the word occurrences during a therapy interaction for supporting a procedure. In addition, it is noted that the scoring platform 115 may be a separate entity of the system 100, or included within the UE 101 (e.g., as part of the applications 103).

In one embodiment, the scoring platform 115 may perform global association rule extraction. For example, the records of one or more patients are confidential, and cannot be globally shared and definitely not in real time. To solve this issue, the scoring platform 115 extracts the association between patient interaction and the evidence that they are progressing or regressing or neutral. The scoring platform 115 may curate the evidence and the inputs that created the evidence, rather than having patients records with all the information attached to it. In other words, the scoring platform 115 may extract a rule, and the rule may be automatically sent for human curation (i.e. therapist), wherein they can validate that particular rules, and that rule may fall into a global association rules which keeps growing, updating, increasing. Such process requires automatic user de-identification, wherein user de-identification allows for patient information to exist on the fly for the purpose of rule extraction and evidence curation. In one scenario, the scoring platform 115 may use the backward feature elimination.

In one embodiment, the scoring platform 115 may implement a bucket-of-models approach. In one scenario, in the process of FAPS scoring, within the fuzzy learner predictor algorithm there may be two or three mechanisms, and a particular model mechanism is chosen at a particular time based on their performance. The mechanisms can optionally include a mix and match of traditional Neural Net, Support Vector Model and associated mining algorithms with Restricted Boltzman Machine and other forms of Deep Belief Networks. The only way of knowing which particular mechanism is working better is by running these mechanisms at the same time, and then the scoring platform 115 may use the bucket-of models approach, and uses the model mechanism that is providing the most optimal convergence to the goal. In other words, it means that the model mechanism which seems to have agreed to the last known position of the progression of the patient or the care recipient is the model that wins. The process does not discard one model mechanism for another; the models are used at the same time to get an optimal goal incentive.

In one embodiment, the scoring platform 115 may cause a pairing of fuzziness associated with evidence to an association, a propensity scoring, a survival statistic, or a combination thereof for classifying FAPS scoring. For example, the survival statistics may be associated with fuzzy algorithms to determine the probability that the generated score is good for a certain time period. For example, on a scale of 0 to 1, a score of 0.8 may be good, but for how long does the score of 0.8 survive before it is no longer valid?

According to exemplary embodiments, end user devices may be utilized to communicate over system 100 and may include any customer premise equipment (CPE) capable of sending and/or receiving information over one or more of networks 107-113. For instance, a voice terminal may be any suitable plain old telephone service (POTS) device, facsimile machine, etc., whereas a mobile device (or terminal) may be any cellular phone, radiophone, satellite phone, smart phone, wireless phone, or any other suitable mobile device, such as a personal digital assistant (PDA), pocket personal computer, tablet, customized hardware, etc. Further, a computing device may be any suitable computing device, such as a VoIP phone, skinny client control protocol (SCCP) phone, session initiation protocol (SIP) phone, IP phone, personal computer, softphone, workstation, terminal, server, etc.

Figure 2A:
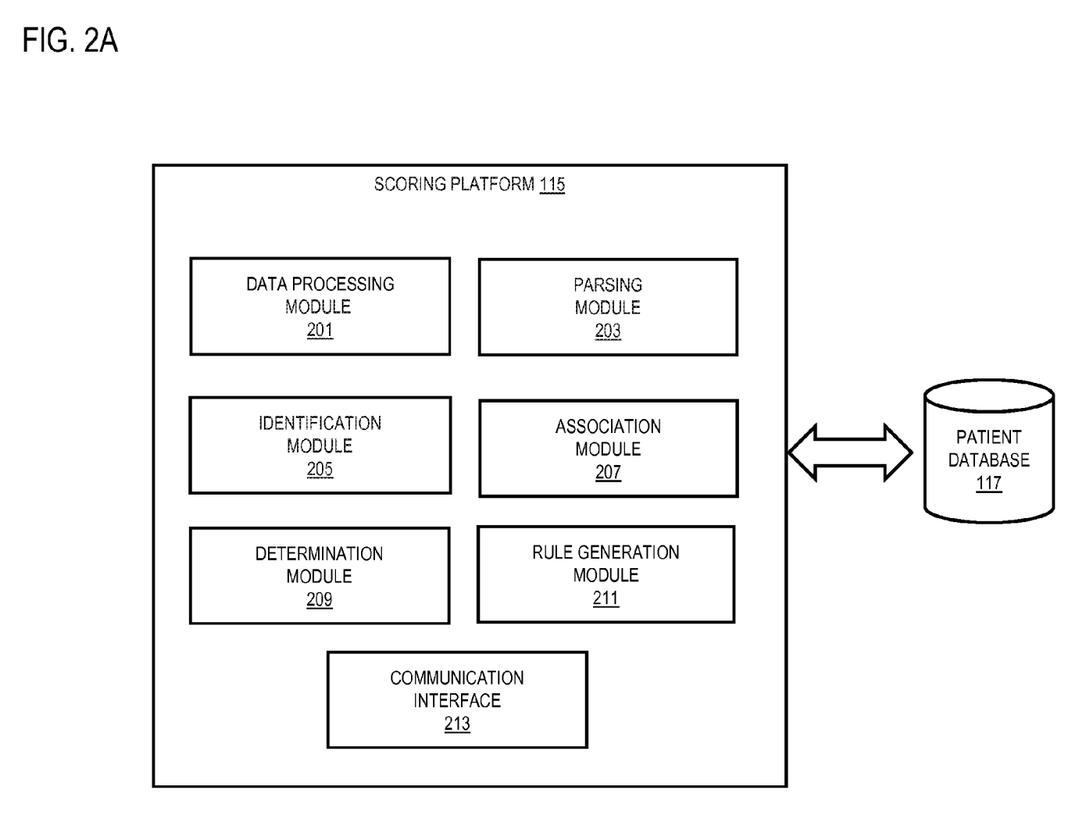
FIG. 2A is a diagram of the components of a scoring platform 115, according to one embodiment.

FIG. 2A is a diagram of the components of the scoring platform 115, according to one embodiment. By way of example, the scoring platform 115 includes one or more components for determining associations and/or propensity among the word occurrences during a therapy interaction for supporting a procedure. It is contemplated that the functions of these components may be combined in one or more components or performed by other components of equivalent functionality. In this embodiment, the scoring platform 115 includes a data processing module 201, a parsing module 203, an identification module 205, an association module 207, a determination module 209, a rule generation module 211 and a communication interface 213.

In one embodiment, the data processing module 201 processes the patient database 117 prior to generating a score for a procedure. In one embodiment, the patient database 117 contains information collected from a test or control group individuals including individuals that are healthy and individuals that have particular diseases or health conditions of interest. By way of example, patient data can span any number of data spaces including the public internet, private device application space, and third party data sources along with enterprise transactional and operational support data. In one example embodiment, a health variable includes any health related clinical measurement or observation about a patient. In some cases, the clinical population data are unstructured data that can be substantial in size (e.g., depending on the number variables, diseases, health conditions, etc.). For example, some clinical population data may track dozens (e.g., 6 or 7 dozen) of health variables for each individual record. In one embodiment, because of the size and unstructured nature of the data, the system 100 can ingest and domain validate the data via an extract, transform, and load (ETL) process. In one embodiment, the processing may include determining distribution bias of a disease or health condition of interest with respect to one or more health variables. It is contemplated that the data processing module 201 may use any textual recognition, image recognition, object recognition, audio recognition, speech recognition, etc. techniques for identifying potential text, images, audio, and the like from relevant data sets.

In one embodiment, the parsing module 203 performs automated and machine learned parsing of captured therapy interaction data to identify one or more word occurrences. For example, synonyms used for a symptom may be automatically parsed. In one scenario, the scoring platform 115 may collect data from an EBP for determining a progression of a therapy procedure on a particular recipient over a pre-determined time period. Then, the parsing module 203 may process the information exchanged during a therapy interaction session to cause, at least in part, a parsing of one or more keywords. In one embodiment, the captured therapy interaction data is parsed using a natural language model.

In one embodiment, the identification module 205 identifies the parsed word occurrences captured during a therapy interaction. In one scenario, the identification module 205 causes an identification of rules of interest to discard idle rules and/or the identity of idle rule donor. In another embodiment, the identification module 205 may identify particular words of interest to add in the selecting criteria for a treatment. In another scenario, the identification of one or more words causes an extraction of association rule cluster to identify conversational term associations by FAPS scoring. This process involves providing fuzzy lift values for extracted association rule clusters based on fuzzy learner models.

In one embodiment, the association module 207 determines correlation between one or more identified words using a fuzzy association analysis and deep belief networks. In one scenario, the association module 207 causes a pairing of fuzziness associated with one or more identified word occurrences.

In one embodiment, the determination module 209 determines a therapy recipient's interaction with a cognitive behavioral therapy, a dialectical behavioral therapy, or a combination thereof. In another embodiment, the determination module 209 determines the propensity of one or more association based on probability analysis. In one scenario, the scoring platform 115 accesses the FAPS scoring based on the determination. Then, the scoring platform 115 causes a scoring of the fuzzy values to determine time based outcome propensity.

In one embodiment, the data processing module 201 then interacts with the rule generation module 211 to generate a rule for a disease or health condition of interest and then upload the rule for execution by the scoring platform 115. In one embodiment, the rule generation module 211 causes a pairing of fuzziness associated with data for EBP to an association, a propensity scoring, a survival statistic, or a combination thereof for classifying a FAPS scoring.

The above presented modules and components of the scoring platform 115 can be implemented in hardware, firmware, software, or a combination thereof. Though depicted as a separate entity in FIG. 1, it is contemplated that the scoring platform 115 may be implemented for direct operation by respective UE 101. As such, the scoring platform 115 may generate direct signal inputs by way of the operating system of the UE 101 for interacting with the applications 103. In another embodiment, one or more of the modules 201-213 may be implemented for operation by respective UEs, as a scoring platform 115. Still further, the scoring platform 115 may be integrated for direct operation with services 107-13, such as in the form of a widget or applet, in accordance with an information and/or subscriber sharing arrangement. The various executions presented herein contemplate any and all arrangements and models.

Figure 2B:
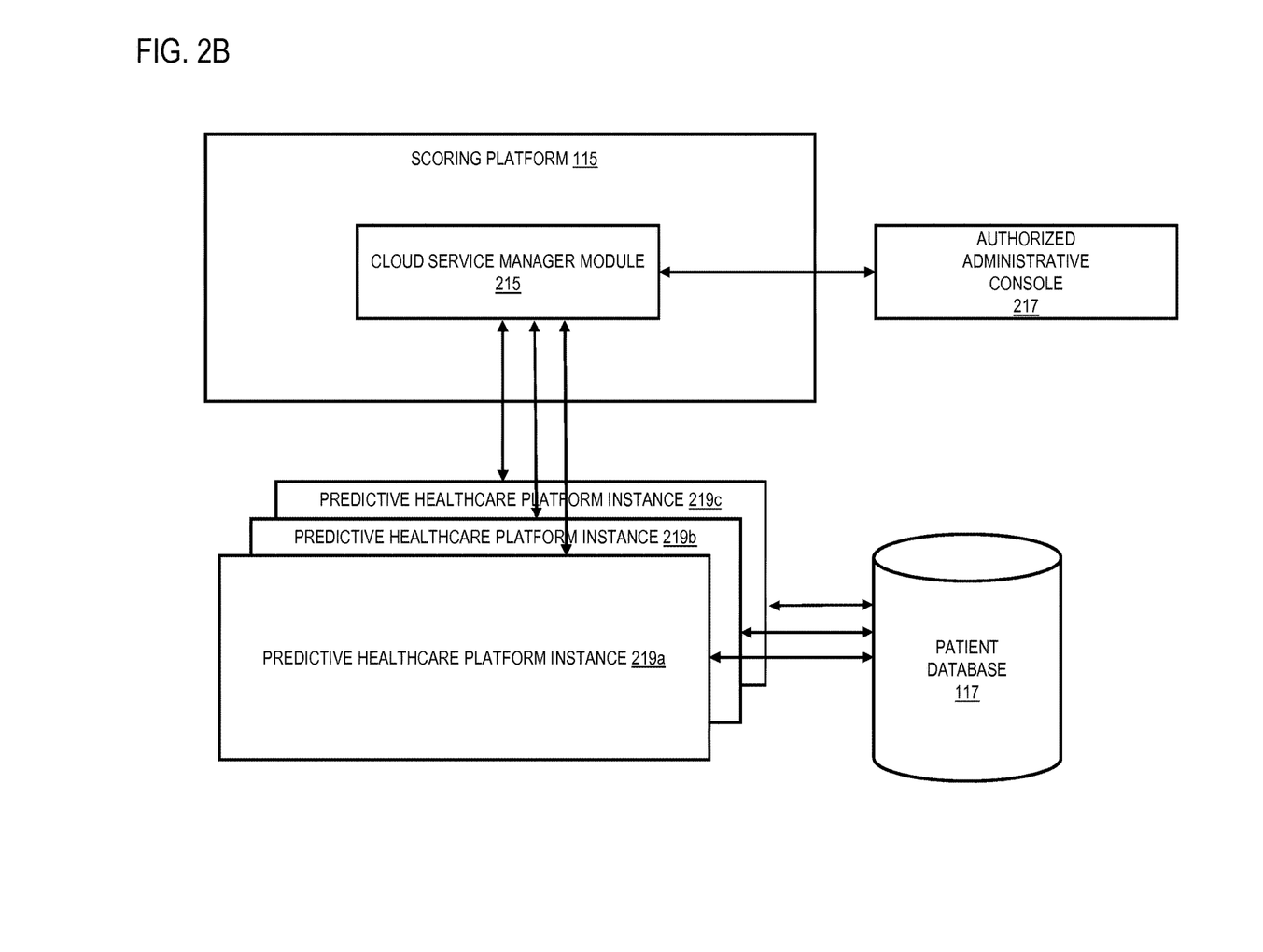
FIG. 2B is a diagram of a system utilizing a scoring platform 115 over a cloud network, according to one embodiment.

FIG. 2B is a diagram of a system utilizing a scoring platform 115 over a cloud network, according to one embodiment. In one embodiment, the scoring platform 115 is controlled by a cloud service manager module 215. The authorized administrative console 217 is used to access the cloud service manager module 215 to use the cloud service manager module 215 to create instances 219a-219c (also collectively referred to as instances 219) of the scoring platform 115 for a channel partner.

The cloud service manager module 215 generates an instance 219 of the scoring platform 115 on demand associated with a channel partner. Each instance 219 of the scoring platform 115 gives the channel partner requesting access through the cloud network (e.g., cloud service 109) the ability to manage the services provided. These services include management of clinical data collection, data processing, disease model generation, rule generation, health classification and scoring, etc.

For example, the channel partner may use collected clinical data to generate ensemble models for predicting health classifications based on patient. This creates an ability to provide predictive health and/or disease classifications.

Figure 3:
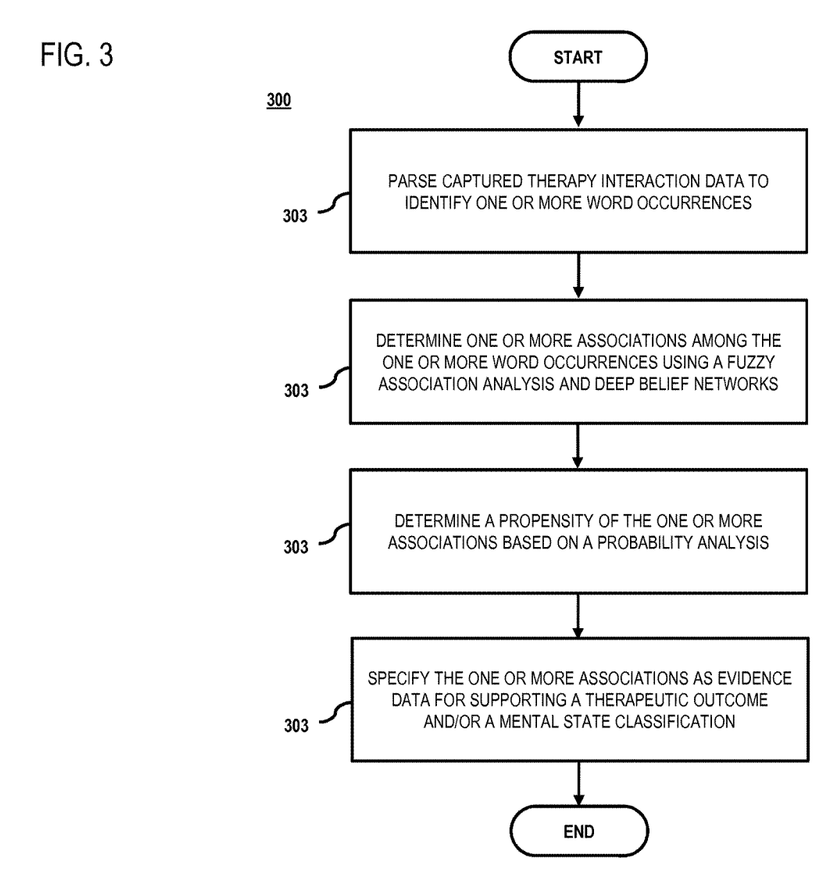
FIG. 3 is a flowchart of a process for determining associations and/or propensity among the word occurrences during a therapy interaction for supporting a procedure, according to one embodiment.

FIG. 3 is a flowchart of a process for FIG. 3 is a flowchart of a process for determining associations and/or propensity among the word occurrences during a therapy interaction for supporting a procedure, according to one embodiment, according to one embodiment.

In step 301, the scoring platform 115 may parse a captured therapy interaction data to identify one or more word occurrences. In one embodiment, the captured therapy interaction data is parsed using a natural language model. In another embodiment, the natural language model supports a DBT methodology, a CBT methodology, or a combination thereof. In one example embodiment, a UE 101 may act as a companion for a user, and the user may talk to the UE 101 as if the UE 101 is a therapist. The UE 101 may identify the words during a communication session for therapy related purposes via speech recognition mechanisms. The UE 101 is specifically using the structures associated with the DBT and CBT therapy, and is participating in the dialogue with natural language.

In step 303, the scoring platform 115 may determine one or more associations among the one or more word occurrences using a fuzzy association analysis and deep belief networks. In one scenario, the association analysis is not relevant to the classification outcome, for example, 100 input variables with n-set tuples. The associations are not classified, but just the possible tuples. The association analysis involves analyzing the associated pairs, for example, (a) this set vs. that set word occurrences; (b) probabilities of combinations occurring; and (c) given the probabilities of outcomes, is it random or is it interesting?

In step 305, the scoring platform 115 may determine a propensity of the one or more associations based on a probability analysis. In one scenario, propensity determination involves determining an input variable implying a set of classification. In one embodiment, the scoring platform 115 may cause a pulling of fuzziness into the propensity analysis to give a time based setting, for example, to determine survival of the propensity.

In step 307, the scoring platform 115 may specify the one or more associations as evidence data for supporting a therapeutic outcome, a mental state classification, or a combination thereof. In one scenario, various procedures are suitable for different people over time, and the procedure changes for people over time based on the input. As a result, the scoring platform 115 may cause a combination of fuzzy associations in an EBP (e.g., psychiatric analysis) to determine the best procedure for a patient.

Figure 4:
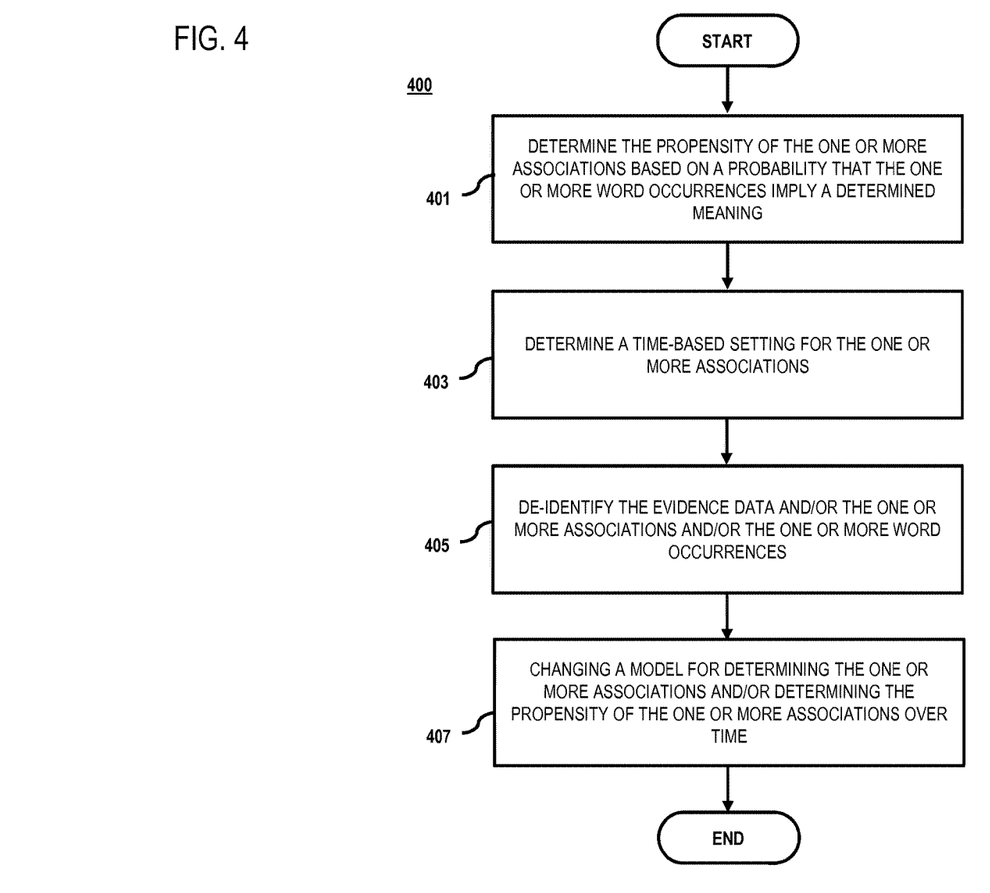
FIG. 4 is a flowchart of a process for determining one or more meanings, a time-based setting, a de-identifying of data, or a combination thereof, according to one example embodiment.

FIG. 4 is a flowchart of a process for determining one or more meanings, a time-based setting, a de-identifying of data, or a combination thereof, according to one example embodiment.

In step 401, the scoring platform 115 may determine the propensity of the one or more associations based on a probability that the one or more word occurrences imply a determined meaning. In one scenario, the scoring platform 115 may take into consideration that similar words when analyzed may not have the same meaning in temporal context (for example, "fine and fine," or "ok and ok"). The scoring platform 115 may provide propensity to determine the fuzziness of what the words actually mean.

In step 403, the scoring platform 115 may determine a time-based setting for the one or more associations, wherein the specifying of the one or more associations as the evidence data is further based on the time-based setting. In one embodiment, the time-based setting includes a survival time. In one example embodiment, the survival time determines the probability that the generated score is good for a certain time period, for example, a score of 0.7 may be good, but the survival time determines the validity of the sore of 0.7.

In step 405, the scoring platform 115 may de-identify the evidence data, the one or more associations, the one or more word occurrences, or a combination thereof prior to a publication, an aggregation, or a combination thereof of the evidence data, the one or more associations, the one or more word occurrences, or a combination thereof. In one scenario, the scoring platform 115 performs global association extraction and evidence curation with automatic user de-identification. In one scenario, the service recipient's (e.g. patient) information may be aggregated and anonymized before adding the information data to the dataset. In one scenario, the datasets may give mental state data for at least one user (e.g. patient).

In step 407, the scoring platform 115 may change a model for determining the one or more associations, determining the propensity of the one or more associations, or a combination thereof over time. In one scenario, the scoring platform 115 may implement the bucket-of-models approach for enhancing rapid convergence and achieving near-optimal goal incentives. In one example embodiment, there may be two or three mechanisms in the process of FAPS scoring, wherein a particular model mechanism is chosen at a particular time based on their performance. In one embodiment, the changing of the model is further based on a contextual parameter associated with a subject of the captured therapy interaction data.

Figure 5:
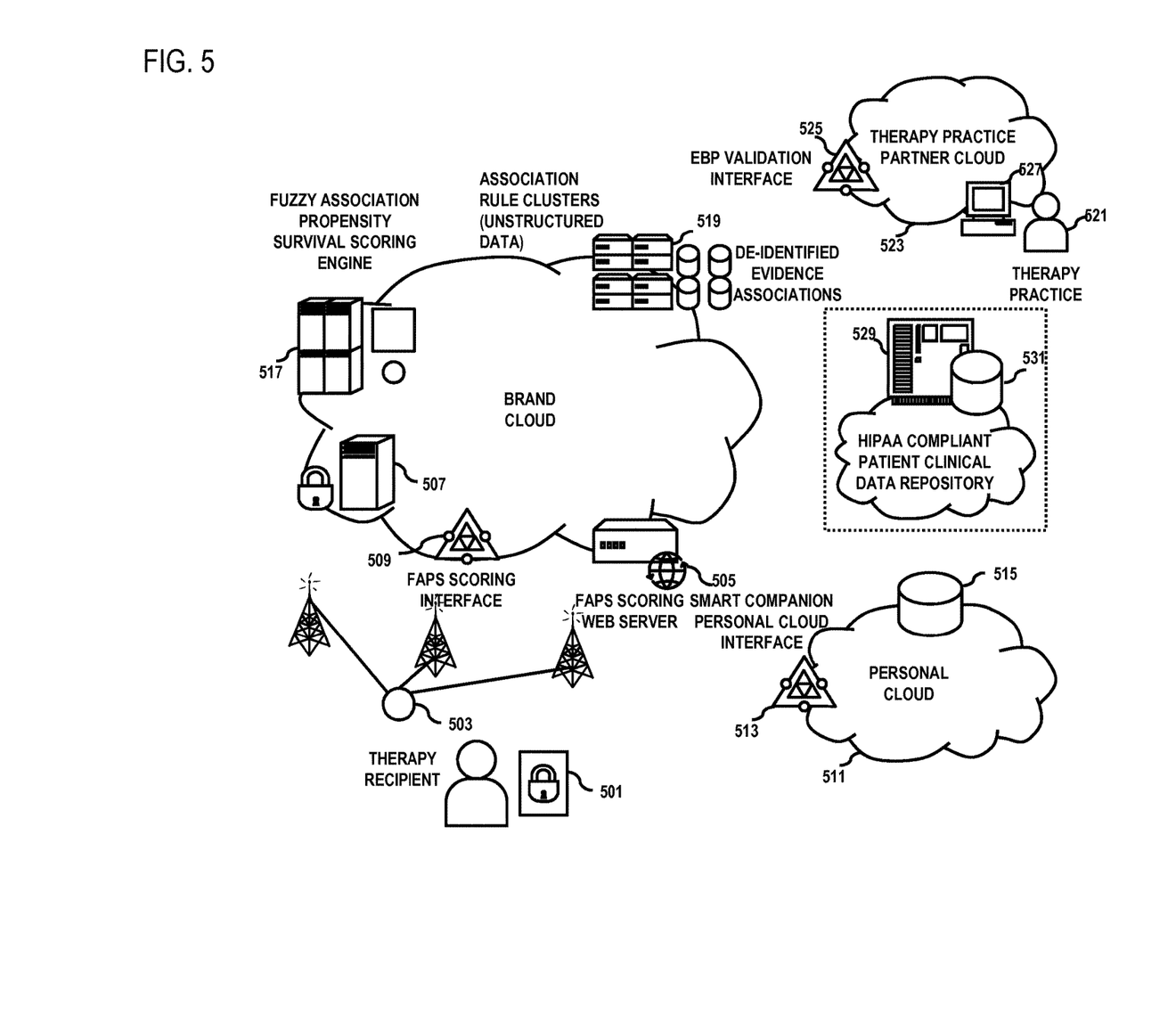
FIG. 5 is a user interface diagram that represents a scenario wherein an enterprise cloud rebrandable white label service that learns and assists EBP, for example, for CBT and/or DBT, according to one example embodiment.

FIG. 5 is a user interface diagram that represents a scenario wherein an enterprise cloud rebrandable white label service that learns and assists EBP, for example, for CBT and/or DBT, according to one example embodiment. In one embodiment, the invention introduces a new automated learning technique to assist with fuzziness associated with EBP in classifying FAPS. In one scenario, a therapy recipient device [501] uses a wireless connection [503] to connect to the FAPS Scoring Web Server [505] and is authenticated via the authentication server to use the FAPS Scoring Interface [509]. Then, the FAPS Scoring Interface [509] deploys a therapy recipient device specific service to the personal cloud [511] that serves as the smart companion personal cloud interface [513] and recipient controlled and operated storage [515]. In one embodiment, the therapy recipient device [501] authenticates via the authentication server and enables creation of personal cloud interface [513] via the FAPS Scoring Interface [509]. Subsequently, the CBT and/or DBT event interactions by the recipient triggers access to the FAPS Scoring Engine [517]. In one embodiment, the DBT and CBT interaction with personal cloud [511] triggers FAPS Scoring on the FAPS Scoring Engine [517] and causes an extraction of the fuzzy associations. The FAPS Scoring Engine [517] identifies conversational term associations and proceeds to provide fuzzy lift values for extracted association rule clusters based on fuzzy learner models. These fuzzy values are then scored to determine time based outcome propensity. The classified outcome is recorded as evidence and both the association rule clusters and the de-identified evidence are linked in the EBP Server [519]. In one scenario, the process of rule clustering involves the association propensity mechanism choosing a rule, for example, there may be numerous rules in terms of the permutations that are possible. Then, the process involves identifying the top rules, and discarding of rules that are not of interest, discarding of the identity of the rule donor etc. In one embodiment, the aggregated de-identified evidence is available for therapy practice [521]. The therapy Practice [521] situated in the therapy partner cloud [523] is able to securely access the EBP Server [519] via the EBP Validation Interface [525] at an authorized display [527] to curate approval of accrued evidence. The providers [529] may directly interact with the recipient to access their data on the recipient controlled storage [515] via the Personal Cloud interface [513] storing raw progress data in a clinical repository [531].

Figure 6:
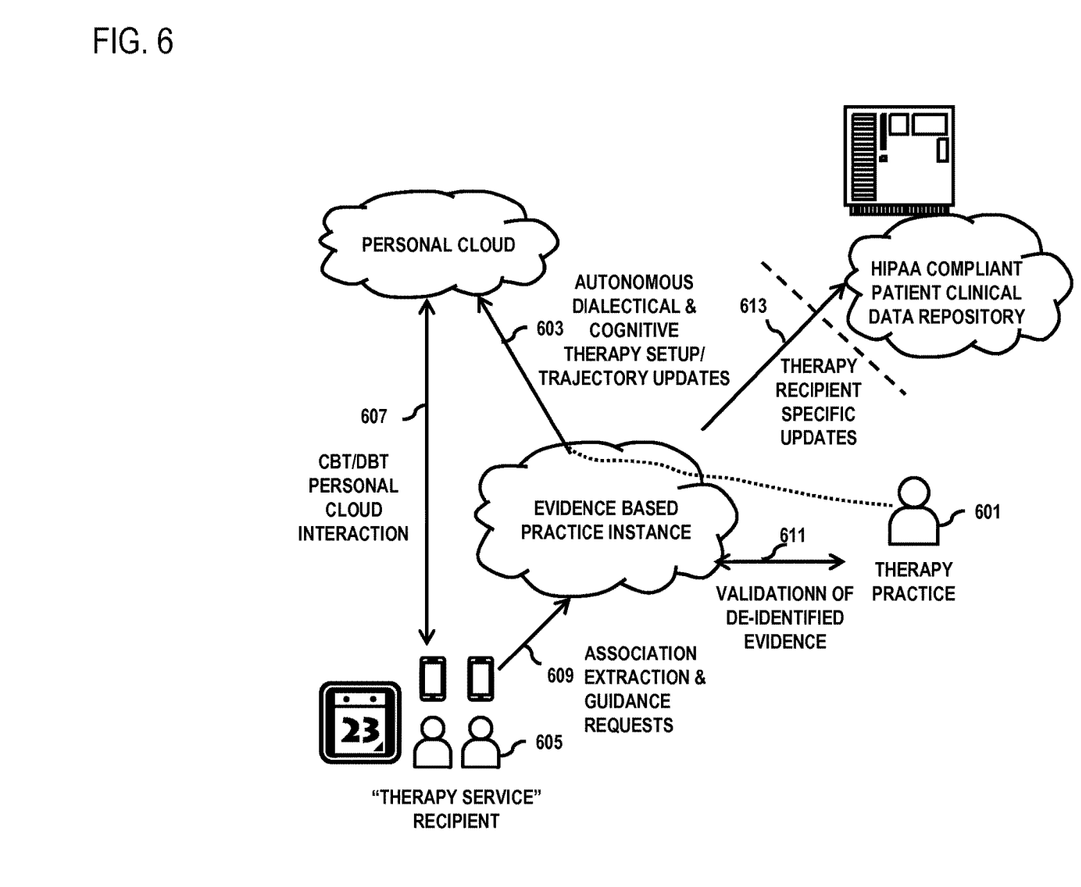
FIG. 6 is a user interface diagram that depicts a CBT and/or a DBT use case flow, according to one embodiment.

FIG. 6 is a user interface diagram that depicts a CBT and/or a DBT use case flow, according to one embodiment. In one embodiment, the initial setup by the therapy practice [601] involves provisioning an autonomous setup/goal trajectory update for DBT and/or CBT natural language interaction [603]. The initial setup by the therapy practice is followed by the recipient interaction, wherein therapy recipient interactions are ingested in personal clouds [607]. Then, the process involves triggering of extraction of association rules based on fuzzy association extraction and propensity scoring of evidence requests by the recipients [609]. Subsequently, the therapy practice may validate evidence linkages which involve de-identification of recipient specific evidence and validation [611]. Finally, the process involves the storage of identifiable data externally. This step involves external upload of the therapy recipient specific prognosis notes [613]. In one example embodiment, the therapist at a therapy service may provision the personal cloud of the therapy service recipient to determine the interaction time in the near future. As soon as the personal cloud is provisioned, the therapy service recipient may start interacting with the personal cloud via their respective UE 101. The therapy service recipient may provide inputs which may result in extraction of these associations based on their interaction. The process of association extractions goes into the could (the EBP where the FAPS scoring happens) and once the rule is extracted, the rule is automatically sent to the therapy practitioners, who then curates it to determine whether the automatically identified rule is correct. Then, the rule goes into the global rule set which may be used for other patients. In one scenario, FIG. 6 represents EBP for individualized care that learns to accommodate fuzziness in patient situational characteristics in extracting prognosis evidence.

Figure 7:
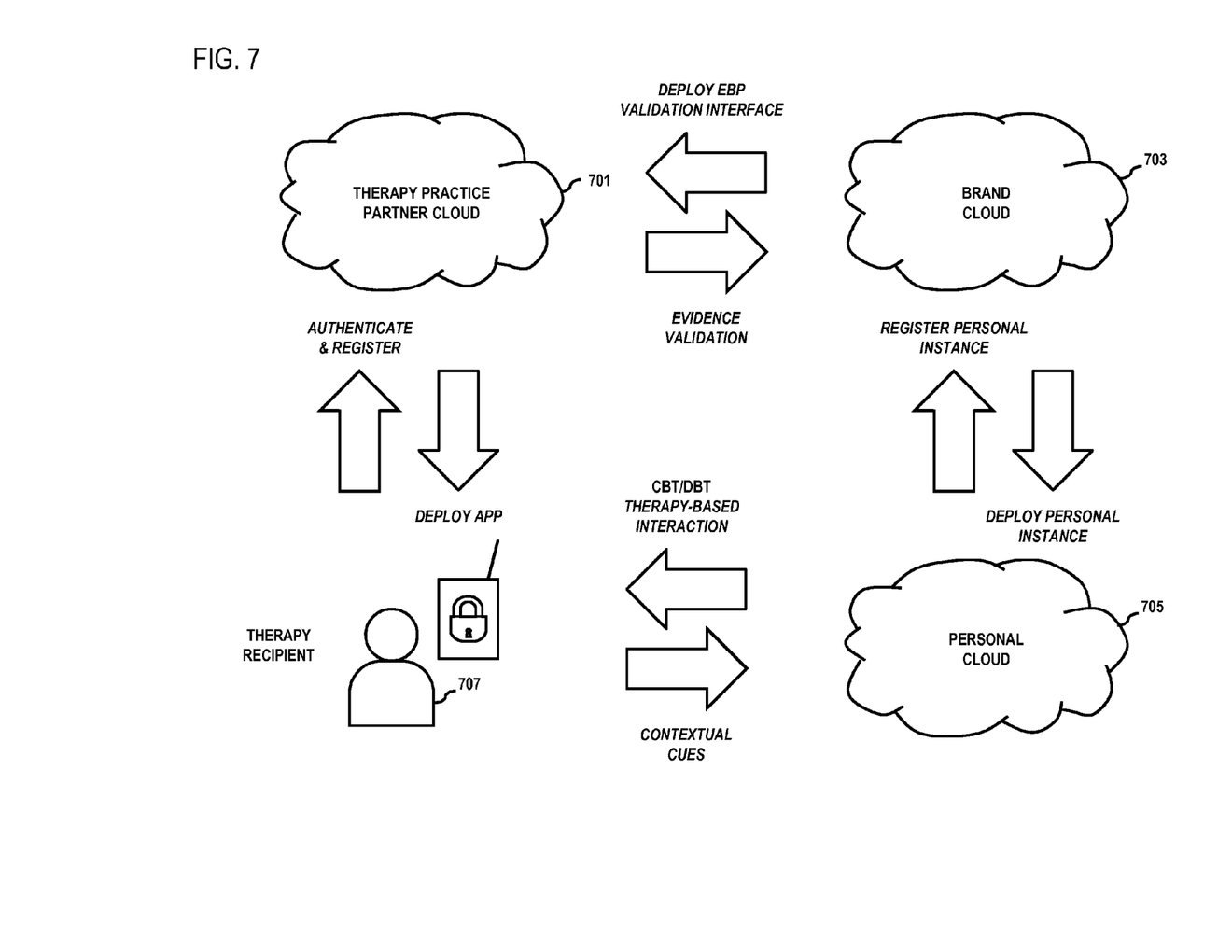
FIG. 7 is a user interface diagram that represents an offering of the EBP as a managed cloud based service, according to one example embodiment.

FIG. 7 is a user interface diagram that represents an offering of the EBP as a managed cloud based service, according to one example embodiment. In one scenario, a business-to-provider-to-consumer (B2P2C) business model is likely to emerge with EBP by incorporating the three key cloud instantiations. The therapy practice Partner Cloud [701] supports the deployment of a domain specific application or a web interface for conducting the CBT and/or DBT interactions. It also serves as the virtual point of provisioning interaction for the personal cloud setup. The validation of evidence occurs via the validation interface instantiated for a particular therapy practice on the cloud [703]. The cloud [703] is where the EBP high speed analysis and linkages occur. The personal cloud [705] serves the recipient both in terms of being an interactive point of service as well as providing consensual access by the provider to the raw prognosis data that is identifiable. The use of FAPS scoring associated with labeling evidence of progress is the key feature of the cloud [703]. The combination of fuzziness and temporal scoring allows for a dynamic learning experience that self-customizes based on the recipient [707] responses while contributing to global knowledge about the efficacy of the ongoing therapy process. Such systematic approach to CBT and/or DBT is manual today. Hence, FAPS scoring introduces an exciting new toolset for the therapy practice to leverage with their recipient population. In one scenario, the therapy practice partner cloud [701] is able to modify three important operational flow associated variables:

(a) How is always-on pervasive connectivity managed for the recipient?

(b) How should insights be mapped or transformed in post-processing for learning?

(c) What pre-processing contextual domains need to be turned on for observing and interactions (i.e. to provide contextual cues)?

Figure 8:
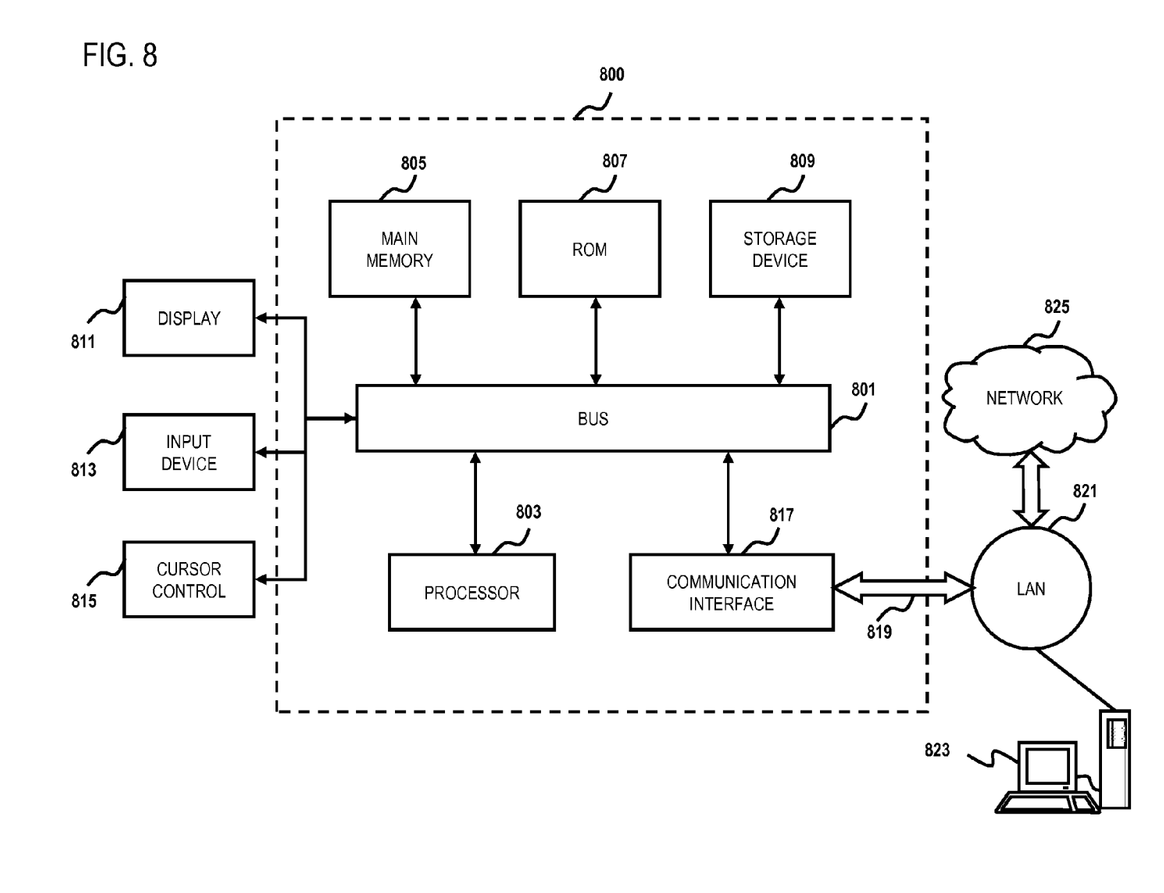
FIG. 8 is a diagram of a computer system that can be used to implement various exemplary embodiments.

The computer system 800 may be coupled via the bus 801 to a display 811, such as a cathode ray tube (CRT), liquid crystal display, active matrix display, or plasma display, for displaying information to a computer user. An input device 813, such as a keyboard including alphanumeric and other keys, is coupled to the bus 801 for communicating information and command selections to the processor 803. Another type of user input device is a cursor control 815, such as a mouse, a trackball, or cursor direction keys, for communicating direction information and command selections to the processor 803 and for controlling cursor movement on the display 811.

According to an embodiment of the invention, the processes described herein are performed by the computer system 800, in response to the processor 803 executing an arrangement of instructions contained in main memory 805. Such instructions can be read into main memory 805 from another computer-readable medium, such as the storage device 809. Execution of the arrangement of instructions contained in main memory 805 causes the processor 803 to perform the process steps described herein. One or more processors in a multiprocessing arrangement may also be employed to execute the instructions contained in main memory 805. In alternative embodiments, hard-wired circuitry may be used in place of or in combination with software instructions to implement the embodiment of the invention. Thus, embodiments of the invention are not limited to any specific combination of hardware circuitry and software. The computer system 800 may further include a Read Only Memory (ROM) 807 or other static storage device coupled to the bus 801 for storing static information and instructions for the processor 803.

The computer system 800 also includes a communication interface 817 coupled to bus 801. The communication interface 817 provides a two-way data communication coupling to a network link 819 connected to a local network 821. For example, the communication interface 817 may be a digital subscriber line (DSL) card or modem, an integrated services digital network (ISDN) card, a cable modem, a telephone modem, or any other communication interface to provide a data communication connection to a corresponding type of communication line. As another example, the communication interface 817 may be a local area network (LAN) card (e.g. for Ethernet™ or an Asynchronous Transfer Model (ATM) network) to provide a data communication connection to a compatible LAN. Wireless links can also be implemented. In any such implementation, the communication interface 817 sends and receives electrical, electromagnetic, or optical signals that carry digital data streams representing various types of information. Further, the communication interface 817 can include peripheral interface devices, such as a Universal Serial Bus (USB) interface, a PCMCIA (Personal Computer Memory Card International Association) interface, etc. Although a single communication interface 817 is depicted in FIG. 8, multiple communication interfaces can also be employed.

The network link 819 typically provides data communication through one or more networks to other data devices. For example, the network link 819 may provide a connection through local network 821 to a host computer 823, which has connectivity to a network 825 (e.g. a wide area network (WAN) or the global packet data communication network now commonly referred to as the "Internet") or to data equipment operated by a service provider. The local network 821 and the network 825 both use electrical, electromagnetic, or optical signals to convey information and instructions. The signals through the various networks and the signals on the network link 819 and through the communication interface 817, which communicate digital data with the computer system 800, are exemplary forms of carrier waves bearing the information and instructions.

The computer system 800 can send messages and receive data, including program code, through the network(s), the network link 819, and the communication interface 817. In the Internet example, a server (not shown) might transmit requested code belonging to an application program for implementing an embodiment of the invention through the network 825, the local network 821 and the communication interface 817. The processor 803 may execute the transmitted code while being received and/or store the code in the storage device 809, or other non-volatile storage for later execution. In this manner, the computer system 800 may obtain application code in the form of a carrier wave.

The term "computer-readable medium" as used herein refers to any medium that participates in providing instructions to the processor 803 for execution. Such a medium may take many forms, including but not limited to non-volatile media, volatile media, and transmission media. Non-volatile media include, for example, optical or magnetic disks, such as the storage device 809. Volatile media include dynamic memory, such as main memory 805. Transmission media include coaxial cables, copper wire and fiber optics, including the wires that comprise the bus 801. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the embodiments of the invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

Figure 9:
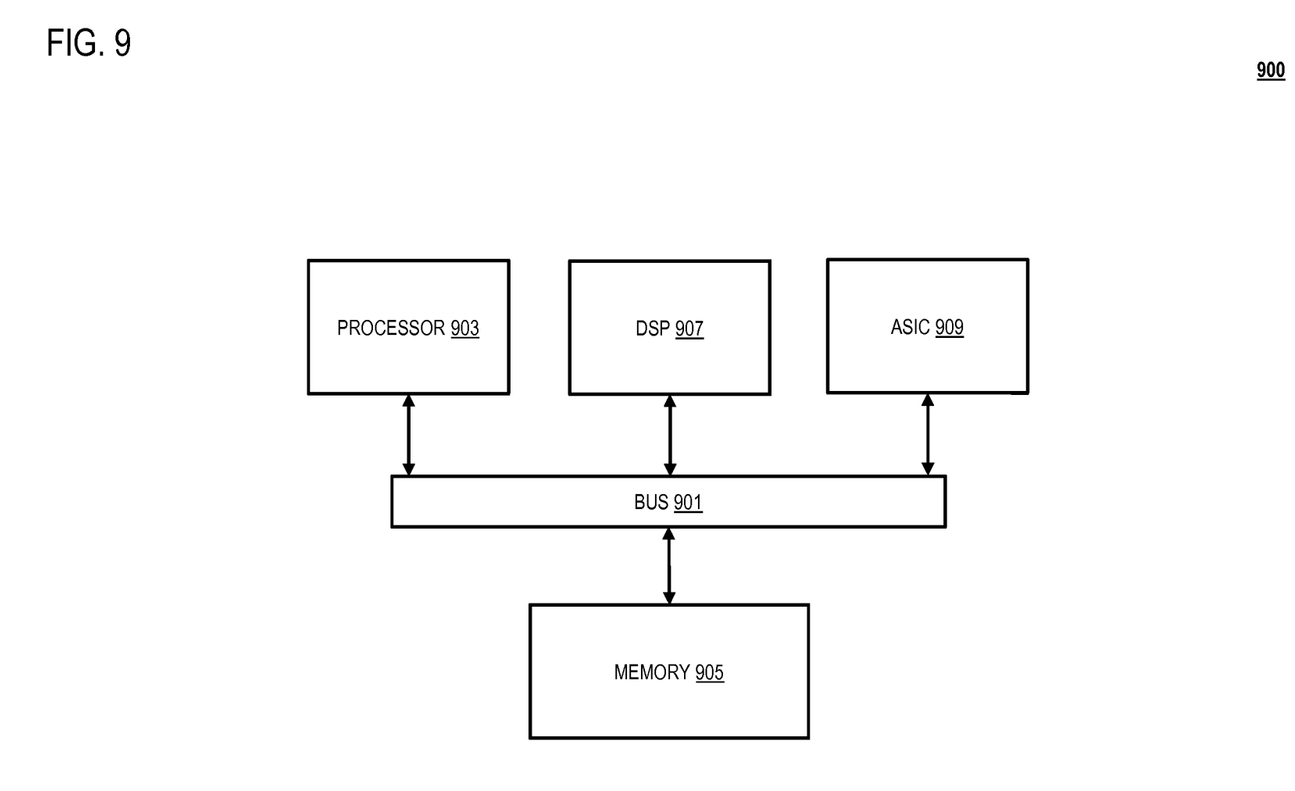
FIG. 9 is a diagram of a chip set that can be used to implement various exemplary embodiments.

FIG. 9 illustrates a chip set 900 upon which an embodiment of the invention may be implemented. Chip set 900 is programmed to present a slideshow as described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 900, or a portion thereof, constitutes a means for performing one or more steps of FIGS. [3-4].

In one embodiment, the chip set 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-world signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform the inventive steps described herein to controlling a set-top box based on device events. The memory 905 also stores the data associated with or generated by the execution of the inventive steps.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method, comprising:
conducting, by a device, a conversation with a patient;
capturing, by the device, therapy interaction data during the conversation, the therapy interaction data including speech uttered by the patient;
parsing, by the device, the captured therapy interaction data to identify one or more word occurrences;
determining, by the device, one or more associations among the one or more word occurrences using a fuzzy association analysis and deep belief networks;
determining, by the device and using fuzzy association propensity survival scoring, a propensity of the one or more associations based on a probability analysis that is based on patient data relating to a plurality of other patients, the patient data including control data that includes:
data relating to one or more healthy patients, and
data relating to one or more patients that have one or more diseases or health conditions; and
determining, by the device and based on the propensity of the one or more associations, whether the patient has the one or more diseases or health conditions.

2. The method of claim 1, further comprising:
determining the propensity of the one or more associations further based on a probability that the one or more word occurrences imply a determined meaning.

3. The method of claim 1, further comprising:
determining a time-based setting for the one or more associations,
wherein the specifying of the one or more associations as the evidence data is further based on the time-based setting, and
wherein the time-based setting includes a survival time of the one or more associations, after which the one or more associations are no longer valid.

4. The method of claim 1, further comprising:
de-identifying evidence data that indicates whether the patient has the one or more diseases or health conditions, the one or more associations, the one or more word occurrences, or a combination thereof prior to a publication of the evidence data, the one or more associations, the one or more word occurrences, or a combination thereof; and
publishing the de-identified evidence data, the one or more associations, the one or more word associations, or the combination thereof, without publishing identifying information of the patient.

5. The method of claim 1, wherein the captured therapy interaction data is parsed using a natural language model.

6. The method of claim 5, wherein the natural language model supports a Dialectical Behavior Therapy (DBT) methodology, a Cognitive Behavioral Therapy (CBT) methodology, or a combination thereof.

7. The method of claim 1, further comprising:
changing a model for determining the one or more associations, determining the propensity of the one or more associations, or a combination thereof over time.

8. The method of claim 7, wherein the changing of the model is further based on a contextual parameter associated with a subject of the captured therapy interaction data.

9. An apparatus, comprising a memory device storing processor-executable instructions; and
a processor configured to execute the processor-executable instructions, wherein executing the processor-executable instructions causes the processor to
conduct a conversation with a patient;
capture therapy interaction data during the conversation, the therapy interaction data including speech uttered by the patient;
parse the captured therapy interaction data to identify one or more word occurrences;
determine one or more associations among the one or more word occurrences using a fuzzy association analysis and deep belief networks;
determine using fuzzy association propensity survival scoring, a propensity of the one or more associations based on a probability analysis that is based on patient data relating to a plurality of other patients, the patient data including control data that includes:
data relating to one or more healthy patients, and data relating to one or more patients that have one or more diseases or health conditions; and
determine, based on the propensity of the one or more associations, whether the patient has the one or more diseases or health conditions.

10. The apparatus of claim 9, wherein executing the processor-executable instructions further causes the processor to:
determine the propensity of the one or more associations further based on a probability that the one or more word occurrences imply a determined meaning.

11. The apparatus of claim 9, wherein executing the processor-executable instructions further causes the processor to:
determine a time-based setting for the one or more associations,
wherein the specifying of the one or more associations as the evidence data is further based on the time-based setting, and
wherein the time-based setting includes a survival time of the one or more associations, after which the one or more associations are no longer valid.

12. The apparatus of claim 9, wherein executing the processor-executable instructions further causes the processor to:
de-identify evidence data that indicates whether the patient has the one or more diseases or health conditions, the one or more associations, the one or more word occurrences, or a combination thereof prior to a publication of the evidence data, the one or more associations, the one or more word occurrences, or a combination thereof; and
publish the de-identified evidence data, the one or more associations, the one or more word associations, or the combination thereof, without publishing identifying information of the patient.

13. The apparatus of claim 9, wherein the captured therapy interaction data is parsed using a natural language model.

14. The apparatus of claim 13, wherein the natural language model supports a Dialectical Behavior Therapy (DBT) methodology, a Cognitive Behavioral Therapy (CBT) methodology, or a combination thereof.

15. The apparatus of claim 9, wherein executing the processor-executable instructions further causes the processor to:
change a model for determining the one or more associations, determining the propensity of the one or more associations, or a combination thereof over time.

16. The apparatus of claim 15, wherein the changing of the model is further based on a contextual parameter associated with a subject of the captured therapy interaction data.

17. A non-transitory computer-readable medium storing a set of processor-executable instructions, which, when executed by one or more processors, cause the one or more processors to:
conduct a conversation with a patient;
capture therapy interaction data during the conversation, the therapy interaction data including speech uttered by the patient;
parse the captured therapy interaction data to identify one or more word occurrences;
determine one or more associations among the one or more word occurrences using a fuzzy association analysis and deep belief networks;
determine using fuzzy association propensity survival scoring, a propensity of the one or more associations based on a probability analysis that is based on patient data relating to a plurality of other patients, the patient data including control data that includes:
data relating to one or more healthy patients, and
data relating to one or more patients that have one or more diseases or health conditions; and
determine, based on the propensity of the one or more associations, whether the patient has the one or more diseases or health conditions.

18. The non-transitory computer-readable medium system of claim 17, wherein the processor-executable instructions further cause the one or more processors to:
determine the propensity of the one or more associations further based on a probability that the one or more word occurrences imply a determined meaning.

19. The non-transitory computer-readable medium system of claim 17, wherein the processor-executable instructions further cause the one or more processors to:
determine a time-based setting for the one or more associations,
wherein the specifying of the one or more associations as the evidence data is further based on the time-based setting, and
wherein the time-based setting includes a survival time of the one or more associations, after which the one or more associations are no longer valid.

20. The non-transitory computer-readable medium system of claim 17, wherein the processor-executable instructions further cause the one or more processors to:
de-identify evidence data that indicates whether the patient has the one or more diseases or health conditions, the one or more associations, the one or more word occurrences, or a combination thereof prior to a publication of the evidence data, the one or more associations, the one or more word occurrences, or a combination thereof; and publish the de-identified evidence data, the one or more associations, the one or more word associations, or the combination thereof, without publishing identifying information of the patient.

* * * * *